United States Patent
Henkin

(10) Patent No.: US 6,701,184 B2
(45) Date of Patent: Mar. 2, 2004

(54) VIRTUAL HOLTER

(75) Inventor: Raphael Henkin, Dana Point, CA (US)

(73) Assignee: Del Mar Reynolds Medical, Inc., Irvine, CA (US)

( * ) Notice: Subject to any disclaimer, the term of this patent is extended or adjusted under 35 U.S.C. 154(b) by 28 days.

(21) Appl. No.: 09/944,846

(22) Filed: Aug. 31, 2001

(65) Prior Publication Data

US 2002/0035336 A1 Mar. 21, 2002

Related U.S. Application Data

(60) Provisional application No. 60/230,520, filed on Sep. 1, 2000.

(51) Int. Cl.[7] .................................................. A61B 5/04
(52) U.S. Cl. ...................................................... 600/523
(58) Field of Search ................................. 600/301, 382, 600/449–450, 481–485, 493–503, 508–527

(56) References Cited

U.S. PATENT DOCUMENTS 6,579,242 B2 * 6/2003 Bui et al. .................... 600/537

* cited by examiner

Primary Examiner—Mark Bockelman
(74) Attorney, Agent, or Firm—W. D. English, Esq.

(57) ABSTRACT

A method for conducting a worldwide, inexpensive and accessible ECG Holter data scanning, processing, and analyzing system by way of obtaining a Holter recording in a conventional manner, then downloading that analog or digital data to a PC, then going online through the PC by way of an ISP, such as DSL, capable of large data transfer, through a USB to tie into a URL web address for a Central Computing Facility with advanced and multifaceted data analysis capability available for short term licensed use, then downloading the Holter data to that URL, then scanning and analyzing the downloaded data at that Central Facility in real time from the remote site, then choosing which alternative analysis sub programs need be run on the stored data, and finally returning the selected Holter analysis to the remote site and tagging, storing, and archiving the raw ECG data and the patient demographics, along with results of the various analyses performed on that data in the Central Facility archives for future access.

6 Claims, 4 Drawing Sheets

VIRTUAL HOLTER

This patent application emanates from a provisional application of the same title and same inventor, Application No. 60/230,520, filed Sep. 1, 2000.

BACKGROUND OF THE INVENTION

1. Field of the Invention

The invention disclosed herein lies in the general field of medical instrumentation and processes. In particular, the invention relates to a method for more expeditious and expansive analysis of Holter data, i.e. a long term, ambulatory electrocardiograph (ECG). More specifically, the invention discloses a Holter analysis process, whereby Holter data accessed from an ambulatory patient in virtually any part of the earth can be submitted by a clinician via a personal computer (PC) through an Internet Service Provider (ISP) over the Internet to a centralized massive computer center where the is clinician can purchase a short term license for proprietary software and hardware to analyze the submitted data in real time and in a variety of processes and formats that might otherwise be too costly to perform. The concept of the Virtual Holter invention is a potentially generic business model for use of the Internet as a means for connecting clinicians world wide to a portal whereby the physician can acquire a short-term license to use sophisticated computer hardware and proprietary software.

2. Description of the Prior Art

The application of ECG data collected from an ambulatory or mobile patient in an uncontrolled ambulatory environment, wherein the data is further analyzed and output in a variety of reports and formats has been in practice since the early 1960's. Known as Holter monitoring the technique is based upon the subject wearing a device that while worn collects ECG data. After a 24 to 48 hour period of continuous ECG recording, the device is removed from the patient, and the storage media (e.g. cassette tape, digital memory, etc.) is further analyzed by a trained clinician in a Holter center with a expensive Holter scanners and analyzers to create a summary document that may be accurately reviewed for diagnostic relevance by a physician or cardiologist.

The recording devices can exist at any clinical site; however, the Holter scanners and analyzers that contain proprietary software modules to summarize the collected data stream are located in clinical facilities or scanning centers that can afford the cost of the software and hardware as well as the technical staff required to operate the Holter system. The data distribution model in its most basic form assumes the collected ECG data makes its way by conventional mail or hand delivered to the site where analysis and reporting occur. The clinician who cannot justify the purchase of the expensive Holter scanners and analyzers has no alternative but to contract a facility capable of performing the analysis of Holter data and to provide a summary report. The accompanying delays in turnaround time of the report delivered by hand or by mail and the multiple parties involved in accessing the relevant reports only adds layers of unnecessary costs and loss of time, personnel intervention and accompanying opportunity for loss of data and error in reports.

A great variety of various wireless or telemetric, remote Holter monitoring devices have been conceived in the prior art that bear some distant relationship to the development of and need for the Virtual Holter invention at hand. U.S. Pat. No. 5,544,661 issued to Davis disclosed an ambulatory ECG monitoring device that tabulated and analyzed data, which data was subsequently transferred by a cell phone to a centralized monitoring and information management system for further evaluation by a clinician or primary physician. U.S. Pat. No. 5,678,562 issued to Sellers describes a similar ambulatory physiological monitor that accumulates data that can be transferred by modem and cellular telephone to a remote PC wherein the PC can in turn operate upon and control the ambulatory monitor. In still another U.S. Pat. No. 5,704,351, Mortara, yet another digital telemetry system is disclosed that transfers by telemetric means up to eight channels of ECG data. In U.S. Pat. No. 5,752,976, Duffin, a worldwide global positioning satellite, patient location and data telemetry system for implantable medical devices is disclosed. The system has the capacity to remotely locate a particular patient with an implanted medical device and can selectively monitor and operate upon a particular device world wide by telemetric means. U.S. Pat. No. 5,944,659, Flach, discloses yet another telemetric system for collection of physiological data that transmits data in real time to a centralized real time data distribution network. In U.S. Pat. No. 6,093,146, Filangeri, a pair of wireless transmission circuits are utilized in a physiological monitoring system, one for transmitting data to a centralized facility and the other acting as a communications link between the patient monitor and a base station.

It should be appreciated that applicant's invention is not a telemetric ECG system; however, the only prior art systems that may relate to applicant's invention by attempting to pass ECG data to a central facility for further analysis by the clinician all relate to telemetric devices. And all of the known telemetry systems have had one or more disadvantages. Telemetry systems are typically designed for use within a limited geographical area, such as a hospital or the home. In past Holter telemetry systems, the patient's mobility is limited, and data is lost if the patient goes outside the coverage area of the system. In addition, telemetry systems transmit raw data continuously, thus requiring a dedicated transmission channel. Furthermore, prior art telemetry systems are relatively complex and expensive to operate.

Although there are numerous telemetric physiological monitoring systems for transmitting long term, ambulatory, physiological or ECG data monitors to a centralized facility for analysis or archival storage, there are no systems transmitting Holter data over a hard wired low cost medium of a local call, telephone interlink world wide, i.e. over the Internet, to a sophisticated computer facility with a wide variety of relevant software whereby one can purchase a limited license to use the centralized computer and proprietary software to perform in real time an analysis of the Holter data in a variety of differing formats and reports. There appears to be a long standing need for the implementation of a system where even very small scale clinics in any part of the world can have immediate access to very expensive computer hardware and relevant sophisticated, proprietary software to make a real time analysis of data in various formats.

SUMMARY OF THE INVENTION

The invention discloses a process for implementing and producing a Holter electrocardiograph anywhere in the world followed up by submitting the recorded data therefrom on a local phone line via a PC or independent modem over the Internet to a centralized and sophisticated Holter data analysis and processing facility where the clinician or physician at a remote facility can periodically purchase a short term license to actively use online, in real time the sophisticated computer hardware and software of the Holter center to conduct a variety of extended and detailed reports of the analysis of the long term, ambulatory ECG data from the remote clinic or medical facility. Many remote facilities around the world may not have sufficient funds and amenities to provide access to expensive, complex, elaborate and sophisticated computer hardware and software to adequately perform a thorough ECG analysis with any great degree of depth and breadth of understanding.

OBJECTS OF THE INVENTION

It is a primary object of the invention to provide an inexpensive and worldwide access (from major urban centers to remote jungle villages) to a large, sophisticated, state of the art, expensive and centralized Holter ECG data scanning, analysis and archiving hardware and software system.

It is another object of the invention to provide a worldwide, real time access to a centralized Holter scanning and analysis service.

DETAILED DESCRIPTION OF A PREFERRED EMBODIMENT

Figure 1:
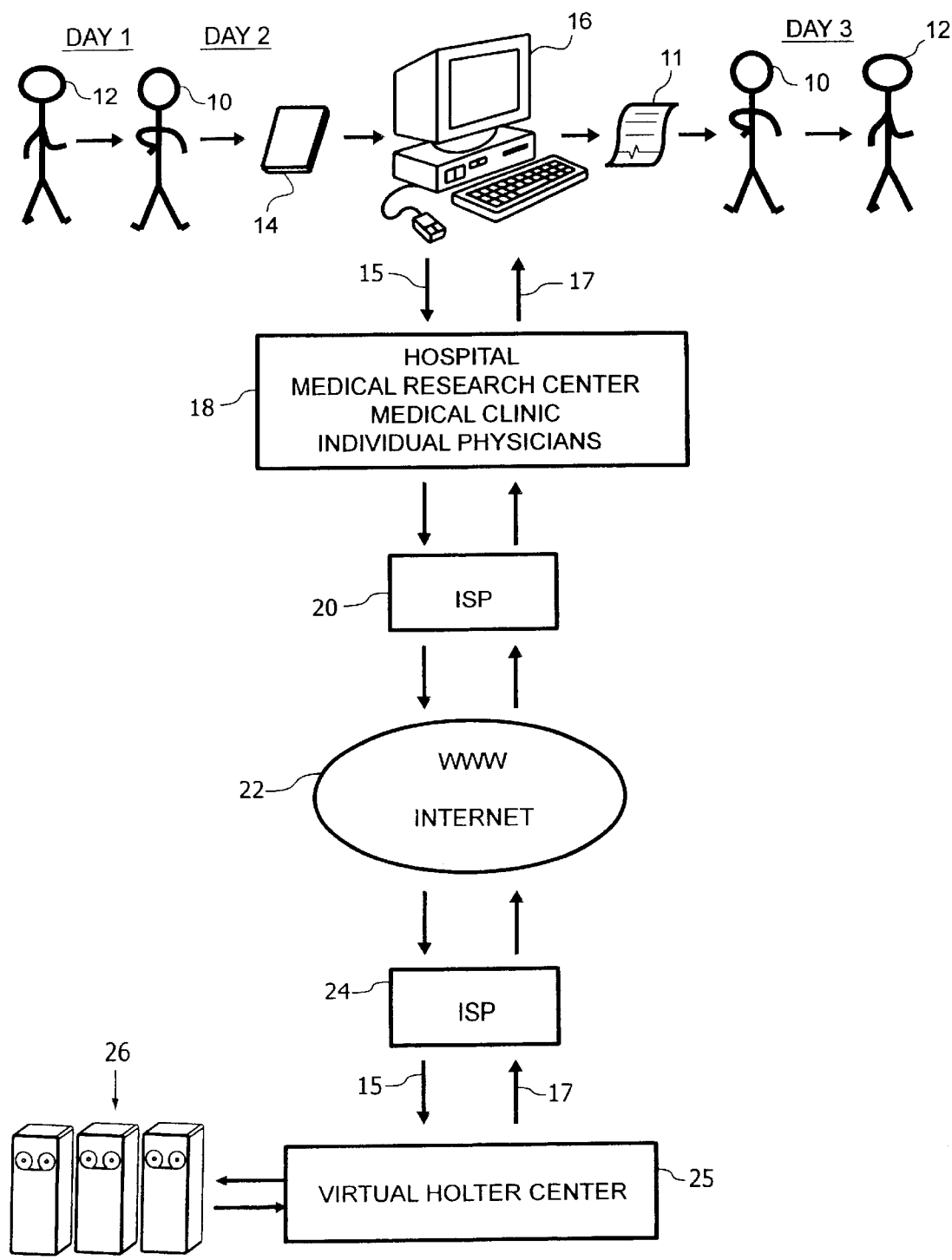
FIG. 1 illustrates a general block flow diagram of the invention process.

In the proposed model, the Virtual Holter, InternetHolter, iHolter process will provide an opportunity for a clinician or physician to download Holter ECG recordings to perform a scan, analysis, review and edit of data collected from patients, without the need to purchase an up to date, complete ECG scanning and analysis system. In the proposed process, the Internet will mediate the transmission and data download process, and costs will be accrued at the centralized Holter facility based upon invocation of the recording for analysis. By such means, a clinician with a small cardiology clientele, that would not justify the purchase of requisite expensive instrumentation and software, would have the capacity to perform tests directly, online and in real time by "renting" or more accurately "obtaining a temporary license" to access a world centralized Holter data scanning and analysis facility, thereby having access to analysis capability in state of the art hardware and software to adequately address his limited and infrequent needs.

Applicant envisions three possible scenarios that a physician might take after performing a lengthy Holter ECG on a patient:

1. A clinician can download a complete Holter recording via a Personal Computer (PC) through an Internet Service Provider (ISP) over the Internet to access the online centralized Holter data scanning and analysis system, thus enabling the physician to scan and analyze ECG in real time on line, and to obtain a complete analysis, review and edit of the data prior to printing the report.
2. The clinician can download an array of post-processing and editing tools from the centralized scanning and analysis system capable of a complete retrospective review of the data. The assumption is that the data will have been previously analyzed.
3. The clinician can be provided with a limited review, edit and commentary application, which would enable a complete overview of pre-analyzed data. The assumption again is that the data will have been previously analyzed.

For each of these scenarios, the proposed website will provide the ability for the clinician to send and upload the ECG data, call for, activate and receive a summarized report from the data, and provide other asset management features as well. The archival of these data will create a digital file for each specific repository tailored to the clinicians needs.

Features for the site are to include:

1. A home page directing the flow of data and data analysis.
2. An education level for the use of the site and its content.
3. A subscriber level for the protected and secure upload and download of pertinent data.
4. A training and help site enabling the clinician to gain assistance in the use of the data analysis system and the applications.
5. An e-commerce level for subscription to application use, as well as enrollment in the asset management abilities.
6. A secondary e-commerce level for the purchase of recording devices and associated accessories.
7. A level dedicated to the subscriber who employs the asset management segment of site.

The foregoing features are part of the proposed site; however, the site is not limited to these features exclusively and may require modifications to address other environments outside the Holter field.

For a more detailed flow diagram of the Virtual Holter process, reference is made to FIG. 1 of the attached Drawing. In FIG. 1, a physician 10 consults with a patient 12 and attaches a long term, ambulatory electrocardiograph recorder (i.e. Holter recorder) 14 to the patient on day 1. The next day on day 2 the completed 24 hour ECG recording of real time ECG analog or digital data "raw Holter data" 15 on recorder 14 taken from the patient and is downloaded to a Personal Computer (PC) terminal 16 in a remote site hospital, medical research center, university, clinic or an individual physician's office 18. The attending physician or clinician would then, by means of the PC modem and Universal Serial Buss (USB) port, go online through his Internet Service Provider (ISP) 20, which preferably should be via an ISDN, DSL, T1–T3, or cable account, i.e. high data transmission account to accommodate the high data transmission capability is needed, then over the Internet/world wide web (WWW) 22 to a "World Centralized Virtual Holter Computer Center or iHolter Center" 25 through its ISP 24. Raw ECG data 15 is passed to a massive, centralized computer hardware facility 26 where the raw Holter data 15 is scanned, processed and analyzed in real time to the attending physician 10 by highly sophisticated and complex proprietary software to yield processed and analyzed Holter ECG data. The attending physician 10 is granted a limited user license each time he logs on, and is thereby granted access for a specified cost per unit time via negotiated contracts between the individual physician, hospital, university, etc. and the Virtual Holter facility. The scan and analysis occurs at the central facility 25 and is observed in real time by the clinician at his remote site sending and receiving PC terminal 16. Alternatively, the clinician my simply download his Holter ECG data over the internet and pay an additional fee to have personnel at the Center 25 perform a specifically requested Holter scan and analysis. In which case, the scanned and analyzed data 17 could be returned within the hour via the reverse path from computer center 26 to Virtual Holter Center 25, to ISP 24, over the Internet 22 to ISP 20 to PC terminal 16 yielding a readable output 19 in the hospital, clinic or physician's office 18 from which the ECG data was submitted. A consulting physician 10 then discusses the analyzed results to the patient on day 3 for a swift, relatively inexpensive Holter diagnosis.

Figure 2:
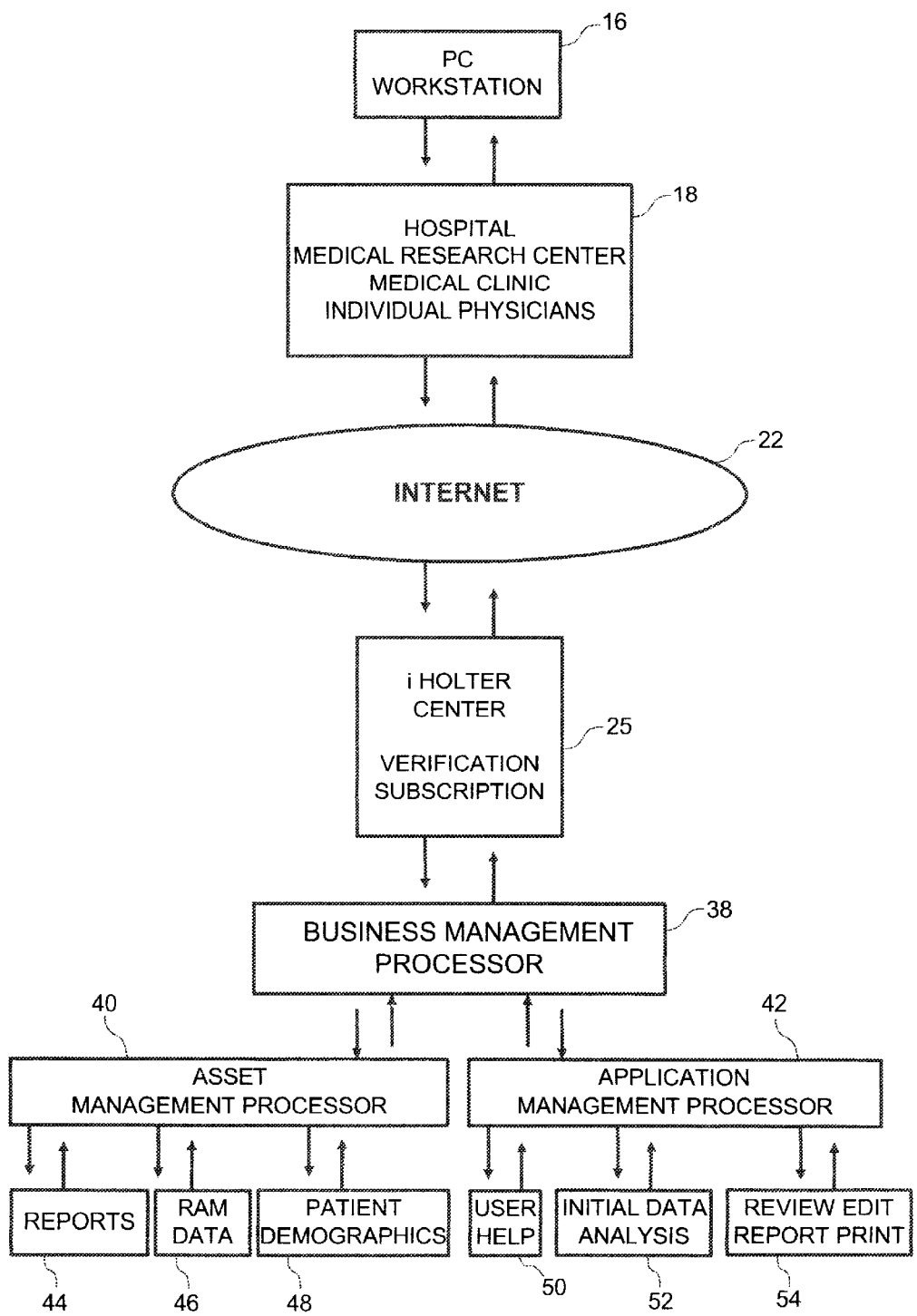
FIG. 2 illustrates a more specific explanation of the invention process.

Referring now to FIG. 2, a more detailed analysis is delineated on the data process distribution at the centralized Holter analysis facility. In FIG. 2 a clinician would be situated at a remote site PC Workstation 16 situated in his office 18 and communicating online over the Internet 22 with a Holter Center 25. At the Holter Center 25, data input/output is time shared and multiplexed through a Business Management processor 38 which directs traffic to either an Asset Management processor 40 or to an Applications Management processor 42. Data and communication as falling under Asset Management are in turn distributed to relative functional categories of Reports 44, RAM data 46 and Patient Demographics 48. Correspondingly, data and communications falling under Applications Management are in turn distributed to functionally relative categories of user help 50, Initial Data Analysis 52, and Review, Edit, Report, and Print process 54.

Figure 3:
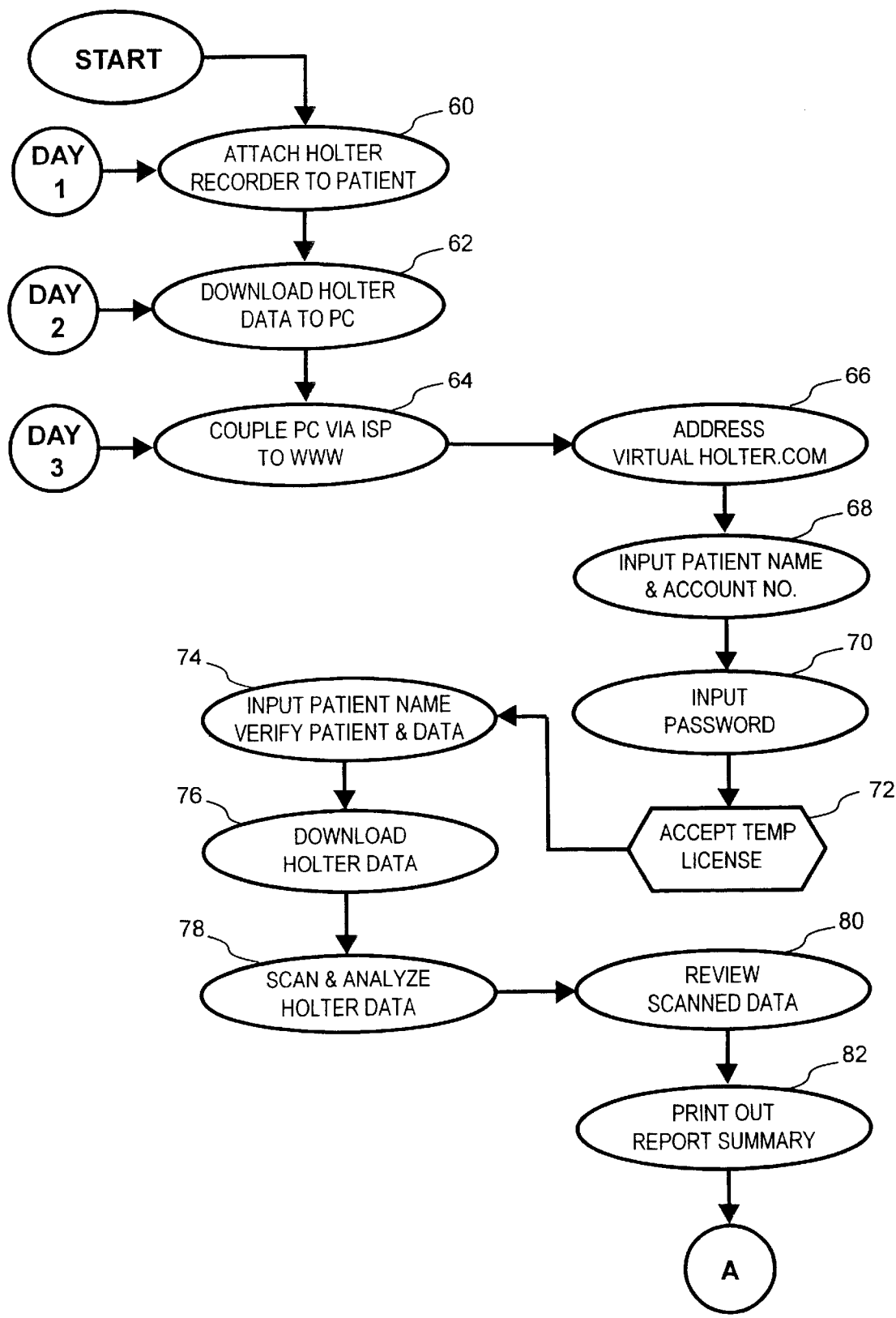
FIG. 3 illustrates a specific process a physician or clinician may use in real time evaluation of an ECG.
Figure 4:
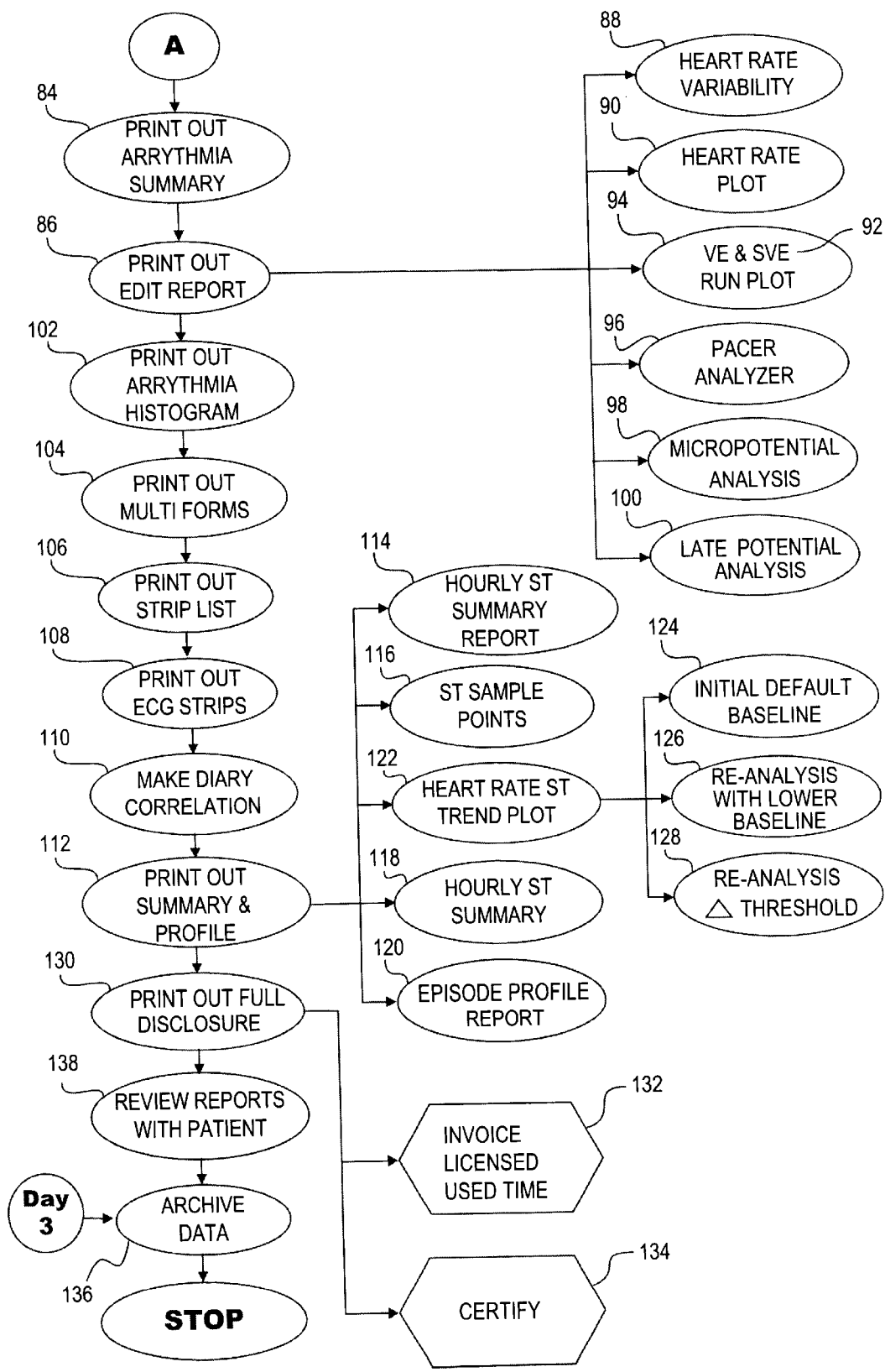
FIG. 4 illustrates a continuation of FIG. 3.

Referring now to FIG. 3, a detailed description of a typical ECG analysis flowchart process that might be utilized by a clinician in real time at the Computer Center 25 from a remote clinic 18 of FIGS. 1 and 2. On day 1, a Holter recorder 14 is attached to an ambulatory patient 12. On day 2, or 24 to 48 hours later, the patient 12 returns to the clinic, the recorder 14 is removed and data therein is downloaded to a PC 16. On the same day or day 3, a clinician at the clinic goes online with the PC 16 to couple the remote computer site with the main frame computers 26 at the Computer Center 25 by means of its URL of VirtualHolter.com 66. Once online, the Computer Center 25 will make inquiry as to the users qualification to enter; client name, account number and pass word must be inserted to be allowed to enter step 70. Upon entering the proper password, the clinician is allowed to pass 70 and must then agree to an on line limited license 72. Now that the clinician is admitted, his computer access billing time commences. The new patient account is now entered by entering patient name and appropriate verification factors 74. At this point the raw Holter data is downloaded 76 is from the remote site computer terminal 16 to the Central Computer Facility 25. Once all Holter data is downloaded, the command for Scan and Analyze is implemented 78. In a few brief minutes the Holter data is scanned before the clinician's eyes on his remote terminal. The command prompt to review scanned data is then made 80 and is followed by a command to print out a report summary 82.

At this point, the clinician may invoke one or all of several proprietary software packages to evaluate different aspects of cardiology interpretation. The clinician may print out an arrhythmia summary 84. The clinician may also print out an "editrend report" 86 which in turn gives rise to related reports: Heart Rate Variability 88, Heart Rate Plot 90, Ventricular Eptopic and Supra Ventricular Eptopic Plots 92 and Run Plots 94, a PaceMaker/Pacer Analyzer report 96, a Micro Potential Analysis report 98, and a Late Potential Analysis report 100. The clinician may then proceed to print out an arrhythmia histogram 102, multiforms 104, strip list 106, ECG strips 108, and a diary correlation 110 can be made with respective ECG PQRST waveform events. The clinician, still in real time over the Internet, can still print out yet other descriptive reports such as the ST Summary and Profile 112. In the ST Summary software, the clinician can also obtain and hourly ST Summary report 114 and ST Sample Points 116, an Hourly ST Summary 118, an Episode Profile report 120, and a ST Heart Rate ST Trend Plot 122 that is further defined by an Initial Analysis Baseline 124, a Reanalysis Lower Baseline 126 and a Reanalysis Delta Threshold 128. At the end of a lengthy ECG analysis, a Full Disclosure print out 130 may be invoked, at which point, i.e. at the termination of any brief or extended analysis process, an invoice for licensed computer use time 132 is processed at the Center and sent immediately to the user along with a Certification 134 as to authenticity of the various aforesaid reports. At the termination of any on line scan and analysis, the data and reports are archived in permanent storage at the Computer Center.

By such means, the clinician/physician can in very short time evaluate and review with the patient 138 a patient's Holter recording and results thereof on the second or third day of the Holter process and archive the raw and processed data at step 136 for future access and use.

I claim:

1. A method for performing a long term, ambulatory electrocardiograph (ECG) Holter data analysis, comprising the following steps:
   accumulating Holter ECG data by conventional Holter means,
   downloading said Holter data to a remote site PC terminal,
   coupling said remote site PC terminal over the Internet to a centralized site Holter computer facility,
   downloading, scanning, and analyzing said Holter data in real time, from said remote site while coupled to said centralized site Holter computer facility, utilizing unique and proprietary software on sophisticated computer hardware at said centralized site on a temporary/limited license use per unit time basis;
   returning processed and analyzed Holter ECG data as said data is being scanned through an identical reverse path over the Internet to said remote site PC terminal, and
   selectively storing said processed data at said centralized site computer facility.

2. A method for performing a Holter diagnosis, comprising the following steps:
   accumulating ECG data by conventional Holter recording means;
   downloading said data to a PC at a remote site;
   coupling the remote site to a large and complex centralized Holter data analysis computer facility through the Internet;
   passing said data from the PC over the Internet to the computer facility;
   scanning and analyzing said data in real time with proprietary software on sophisticated computer hardware at the computer facility, wherein the software grants a temporary/limited license use per hour basis;
   returning processed and analyzed ECG data as it is being scanned and analyzed by an identical reverse path over the Internet to the PC at the remote site; and
   disclosing a Holter analysis by conventional discussion means to the patient.

3. A method for performing a Holter ECG diagnosis, comprising the following steps:
   accumulating ECG data by conventional Holter means for recording from an ambulatory patient at a Remote Site;

downloading said ECG data to a PC terminal at said Remote Site;

coupling said Remote Site PC terminal to a Centralized Computer Facility through the Internet for Holter data scan, process, and analysis of said ECG data;

passing said ECG data from said Remote Site PC terminal over the Internet to said Centralized Computer Facility;

scanning, processing and analyzing said ECG data at said Centralized Computer Facility with proprietary software on sophisticated computer hardware at said Centralized Computer Facility while concomitantly monitoring the process in real time at said Remote Site PC terminal, by means of a purchased and temporary license to use said proprietary software on a per unit time basis; and returning scanned, processed and analyzed ECG data by an identical reverse path over the Internet to said Remote Site PC.

4. A method for performing Holter ECG data analysis according to claim 3, wherein said scanned, processed, and analyzed data is returned to said Remote Site PC during the monitored analysis process.

5. A method for performing Holter ECG data analysis according to claim 5, wherein said scanned, processed, and analyzed data is returned to said Remote Site PC at a later date.

6. A method for performing Holter ECG data analysis according to claim 5, wherein said scanned, processed, and analyzed data is archived at said Centralized Computer Facility for future evaluation, comparison and access.

* * * * *